United States Patent [19]

Gobbini et al.

[11] Patent Number: 5,596,110
[45] Date of Patent: Jan. 21, 1997

[54] PROCESS FOR THE PREPARATION OF 3 β, 14 β-DIHYDROXYETHIANALDEHYDE

[75] Inventors: Mauro Gobbini, Mercallo; Marco Torri, Rho, both of Italy

[73] Assignee: Sigma-Tau Industrie Farmaceutiche Riunite S.p.A., Rome, Italy

[21] Appl. No.: 405,354

[22] Filed: Mar. 16, 1995

[30] Foreign Application Priority Data

May 26, 1994 [IT] Italy ................. RM94A0330

[51] Int. Cl.$^6$ ................. C07J 75/00; C07J 3/00
[52] U.S. Cl. ................. 552/610
[58] Field of Search ................. 552/610

[56] References Cited

PUBLICATIONS

J. S. Boutagy et al. "Cardenolide Analogues". *Aust. J. Chem.*, 24, pp. 2723–2728. 1971. Articles in German. No translations provided. Considered to the extent possible.

Claus Lindig. "Synthese 22–O–Substituierter Cardenolide Sowie Untersuchungen Über Den Oxidativen Abbau Von Cardenoliden Mit Kaliumpermanganat". *Journal F. Prakt. Chemie. Chem*, 328, pp. 682–694. 1986. Articles in German. No translations provided. Considered to the extent possible.

Von M. Schüpbach et al. "Umsetzung Von 3–O–Acetyl–14–Anhydrodigitoxigenin Und 3–O–Acetyl-digitoxigenin Mit Osmiumtetroxid". *Helvetica Chimica Acta*, vol. 54, pp. 2007–2016. 1971. Articles in German. No translations provided. Considered to the extent possible.

*Primary Examiner*—Kimberly J. Prior
*Attorney, Agent, or Firm*—Oblon, Spivak, McClelland, Maier & Neustadt, P.C.

[57] ABSTRACT

An improvement in a process for producing 3β,14β-dihydroxyethianaldehyde is disclosed wherein the oxidation of the lactone ring of digitoxigenin-3-acetate is conducted with an alkaline periodate in the presence of a catalytic amount of ruthenium tetroxide obtained in situ by reacting $RuO_2$ hydrate or $RuCl_3$ with the alkaline periodate.

2 Claims, No Drawings

PROCESS FOR THE PREPARATION OF 3 β, 14 β-DIHYDROXYETHIANALDEHYDE

The present invention relates to an improved process for the preparation of 3β,14β-dihydroxyethianaldehyde

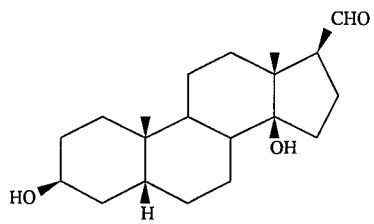

the utility of which is known to be useful as an intermediate for the preparation of anti-hypertensive drugs.

Various syntheses are already known for the preparation of 3β,14β-dihydroxyethianaldehyde. These syntheses, however, present serious drawbacks, such to make them difficult to apply on the industrial scale. The most known synthesis utilized and described in literature (see for example: Boutagy J. S. and Thomas R. E., Aust. J. Chem. 1971, 24, 2723) is based on the oxidation of the lactone ring of digitoxigenin 3-acetate with ozone: the subsequent steps contemplate the reduction, usually with zinc in acetic acid, of the thus formed ozonide to ketone derivative B (see the reaction scheme R=COCHO), reduction of B to tetrol C with sodium borohydride and finally, after the basic hydrolysis of the acetoxy group at position 3, oxidation of the tetrol with sodium periodate to give the desired aldehyde (the overall yield on the raw material is around 80%).

Another method of synthesis, less productive in terms of yield, described in the literature (see for example: Lindig C., J. Prakt. Chem. 1986, 328, 682) foresees the oxidative degradation of the α,β-unsaturated lactone ring with $KMnO_4$ to give 3β-acetoxy-14β-hydroxyethianic acid of Formula I as the main product; the carboxylic group can then be reduced to alcohol and subsequently oxidized to give 3β,14β-dihydroxyethianaldehyde. In the reaction with $KMnO_4$ the ketolactone of Formula II is also formed as by-product. If one wants to transform it to 3β-acetoxy-14β-hydroxyethianic acid of formula I, the ketolactone must be oxidized with $H_2O_2$ in acetic acid: this reaction, besides giving a poor yield, causes safety problems due to the possible formation of potential unstable and explosive peracids.

3β,14β-dihydroxyethianaldehyde can also be obtained from the dihydroxy derivative of formula III, which is obtained by reacting digitoxigenin 3-acetate with osmium tetroxide (Schfipbach M., Krasso A. F., Binder M. and Tamm C., Helv. Chim. Acta 1971, 54, 2007), which however must be used in stoichiometric amounts; catalytic amounts of osmium tetroxide, which must be continuously regenerated by another oxidant present in the reaction mixture, do not allow valuable yields of the sought after product to be obtained. Further, osmium tetroxide is a highly toxic ($LD_{50}$ in mice: 162 mg/Kg by oral administration) and very expensive compound.

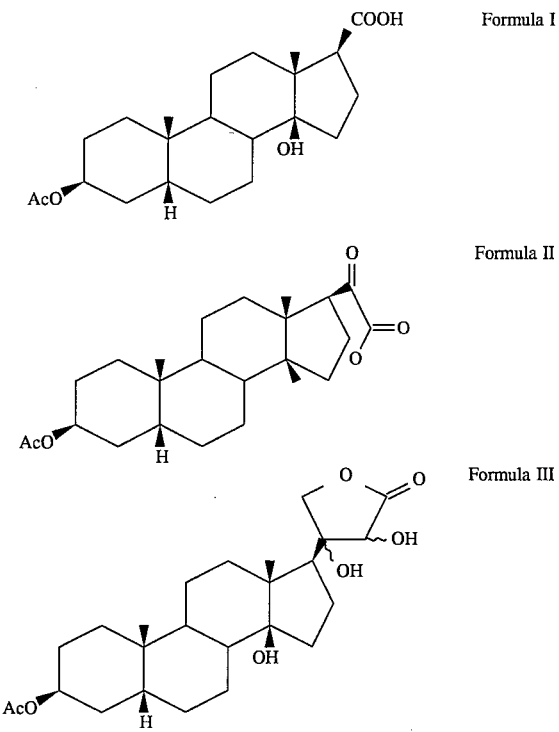

The process according to the present invention is illustrated in the following reaction scheme 1.

Reaction scheme

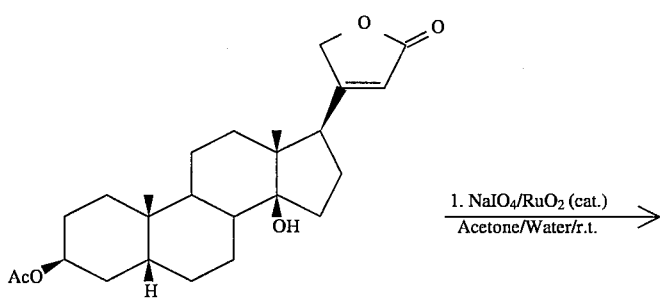

1. $NaIO_4/RuO_2$ (cat.)
   Acetone/Water/r.t.

A: digitoxigenin 3-acetate

-continued
Reaction scheme

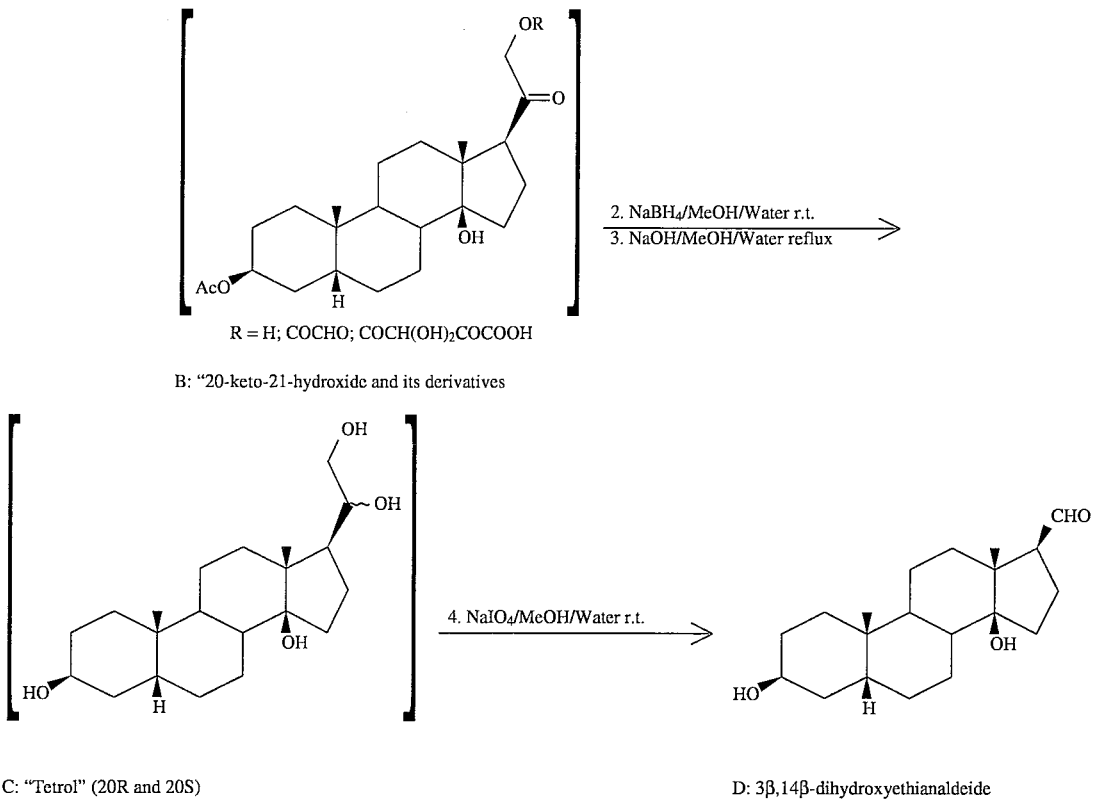

B: "20-keto-21-hydroxide and its derivatives"

C: "Tetrol" (20R and 20S)

D: 3β,14β-dihydroxyethianaldeide

Also, the process according to the invention foresees similarly to the synthesis with ozone, the oxidation of the α,β-unsaturated lactone ring of digitoxigenin 3-acetate A to give the keto derivative B; the subsequent reduction of B with sodium borohydride and hydrolysis of the ester groups present at positions 3 and 21 in a basic environment to give the tetrol C and, finally, the oxidation of such tetrol to 3β,14β-dihydroxyethianaldehyde with alkaline periodates.

The process of the present invention is, however, characterized insofar as the oxidation of the lactone ring of digitoxigenin-3-acetate occurs by means of alkaline periodates in the presence of a catalytic amount of ruthenium tetroxide ($RuO_4$). The ruthenium tetroxide is not added as such to the reaction mixture but is obtained directly in situ by reacting $RuO_2$ hydrate or $RuCl_{13}$ hydrate with an alkaline periodate.

It has been found that the process according to the invention presents remarkable advantages over the prior art synthesis methods.

In fact:

(1) the various reactions or process steps are consecutively performed, in the same reactor, without the need to isolate or purify the intermediate products B and C;

(2) both yield and purity of 3β,14β-dihydroxyethianaldehyde are superior to those achieved with the known syntheses;

(3) the use of toxic substances (such as osmium tetroxide) and formation of potentially dangerous compounds because of their explosiveness, such as the ozonides, which form as intermediates in the synthesis based on the oxidation of the digitoxigenin 3-acetate with ozone, are avoided.

The advantages in terms of costs, time and safety, attainable with the process of the invention are, therefore, apparent.

The process of the present invention is further illustrated by the following example.

EXAMPLE

To a solution of digitoxigenin 3-acetate A (100.0 g) in 3 L of acetone kept under stirring, at room temperature, an aqueous solution of 128.5 g of $NaIO_4$ and 0.4 g of $RuO_2 \cdot 2H_2O$ was added. After 30 minutes, an aqueous solution of 128.5 g of $NaIO_4$ and 0.4 g of $RuO_2 \cdot 2H_2O$ was added (the temperature rose to 40°–45° C.); after 15 minutes from the latter addition 80 mL of isopropanol were added and the resulting mixture was stirred for 15 minutes.

The solid thus formed was filtered and washed directly on the filter with acetone which was then distilled off under reduced pressure; a suspension was thus obtained to which 1.5 L of methanol were added. The pH of the resultant suspension was adjusted to about 7 with 50% NaOH.

11.0 g of $NaBH_4$ dissolved in 300 mL of methanol were added to this suspension and the resulting reaction mixture was stirred for 1 hour (the temperature rose spontaneously to 30°–35° C.).

50.0 g of NaOH in tablets were added and the reaction mixture was kept under reflux conditions for 1 hour. After cooling at room temperature, the pH was adjusted to about 6 with conc. HCl and 90.0 g of $NaIO_4$ were added under stirring to the suspension. The temperature rose spontaneously to about 30° C.

After one hour the solid was filtered off and washed on the filter with ethyl acetate. To the combined filtrates 1 L of water was added. The two phases were separated, the aqueous phase was extracted once again with ethyl acetate and the organic phase was washed consecutively with a saturated NaCl solution containing ascorbic acid (4 g/L), with a saturated NaCl solution containing $NaHCO_3$ (50 g/L) and finally with a saturated NaCl solution. The organic phase was then dehydrated with anhydrous $Na_2SO_4$ and the solvent evaporated under reduced pressure. 73.5 g (95.6%) of 3β,14β-dihydroxyethianaldehyde were obtained as a white foamy solid, purity about 97%.

A 10 g sample was crystallized from acetonitrile/water 7/3 (3 mL/g) to give 8.5 g of aldehyde, melting point 148°–151° C.

IR: $\nu$max (KBr):3600–3200 (OH); 1705 (CHO) $cm^{-1}$.
1H-NMR ($CDCl_3$, δ p.p.m.): 0,97 (s, 19-$CH_3$); 1,04 (s, 18-$CH_3$); 4,14 (m, 3-CH); 9,73 (d, J 3,8 Hz, 20-CHO). MS: m/z 320 ($M^+$).

We claim:

1. In a process for the production of 13β,14β-dihydroxyethianaldehyde comprising the steps of (a) oxidizing the α,β-unsaturated lactone ring of digitoxigenin 3-acetate of formula A

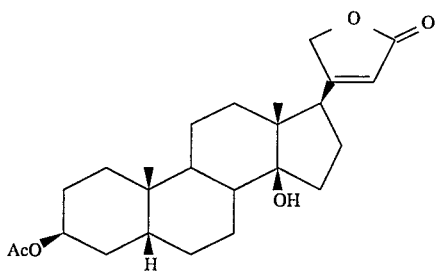

to obtain the keto derivative of formula B

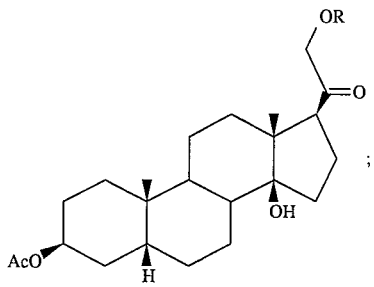

(b) reducing the keto derivative of formula B with sodium borohydride and then hydrolyzing the 3 position and 21 position ester groups to obtain a tetrol of formula C

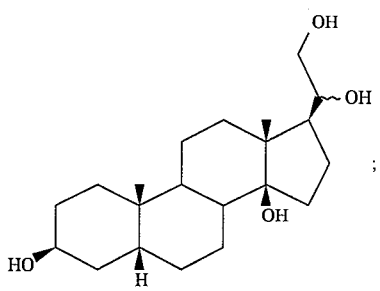

and (c) oxidizing the tetrol of formula C with an alkaline periodate to obtain said 13β,14β-dihydroxyethianaldehyde, the improvement comprising carrying out the oxidation of step (a) by reaction at room temperature with an alkaline periodate in the presence of a catalytic amount of ruthenium tetroxide which is formed in situ from $RuO_2$ hydrate or $RuCl_3$ hydrate.

2. The process of claim 1, characterized in that the steps (a), (b) and (c) are carried out consecutively without isolating and purifying the intermediate compounds B and C.

* * * * *